(12) United States Patent
Haikala et al.

(10) Patent No.: US 6,878,702 B2
(45) Date of Patent: Apr. 12, 2005

(54) ANTI-INFLAMMATORY AGENTS

(75) Inventors: Heimo Haikala, Espoo (FI); Minja Hyttilä-Hopponen, Vantaa (FI); Erkki Nissinen, Espoo (FI); Minna Ruotsalainen, Helsinski (FI); Aino Pippuri, Espoo (FI); Kari Lönnberg, Turku (FI)

(73) Assignee: Orion Corporation, Espoo (FI)

( * ) Notice: Subject to any disclaimer, the term of this patent is extended or adjusted under 35 U.S.C. 154(b) by 0 days.

(21) Appl. No.: 10/416,713

(22) PCT Filed: Nov. 16, 2001

(86) PCT No.: PCT/FI01/01000

§ 371 (c)(1),
(2), (4) Date: Sep. 11, 2003

(87) PCT Pub. No.: WO02/40025

PCT Pub. Date: May 23, 2002

(65) Prior Publication Data

US 2004/0029870 A1 Feb. 12, 2004

(30) Foreign Application Priority Data

Nov. 17, 2000 (FI) .............................. 20002525

(51) Int. Cl.$^7$ .......................... A61K 31/50; A61K 31/54
(52) U.S. Cl. ........................ 514/222.5; 514/247; 544/8; 544/239
(58) Field of Search .............................. 514/222.5, 247; 544/8, 239

(56) References Cited

U.S. PATENT DOCUMENTS 5,185,332 A * 2/1993 Haikala et al. .......... 514/222.5

FOREIGN PATENT DOCUMENTS

| EP | 0 383 449 B1 | 8/1990 |
| EP | 0 565 546 B1 | 10/1993 |
| WO | WO 99/53024 | 10/1999 |

OTHER PUBLICATIONS

Jouko Levijoki et al., "Further Evidence for the Cardiac Troponin C Mediated Calcium Sensitization by Levosimendan: Structure–response and Binding Analysis with Analogs of Levosimendan", J. Mol. Cell Cardiol, vol. 32, Mar. 1, 2000, pp. 479–491.

Elaine J. Tanhehco, "Potassium channel modulators as anti–inflammatory agents", Expert Opin. Ther. Patents, vol. 11, no. 7, Jul. 2001, pp. 1137–1140.

Dalia M. Kopustinskiene et al., "Levosimendan is a mitochondrial $K_{ATP}$ channel opener", European Journal of Pharmacology, vol. 428, No. 3, 2001, pp. 311–314.

Andre Terzic et al., "Mitochondrial $K_{ATP}$ Channel: Probing Molecular Identity and Pharmacology", J. Mol. Cell Cardiol, vol. 32, no. 11, Nov. 2000, pp. 1911–1915.

K. H. Buchheit et al., "$K_{ATP}$ Channel Openers for the Treatment of Airways Hyperractivity", Pulmonary Pharmacology & Therapeutics, vol. 12, 1999, pp. 103–105.

Abstract of S. Antila et al., "Studies on psychomotoric effects and pharmacokinetic interactions of the new calcium sensitizing drug levosimendan and ethanol", Arzneim. Forsch.(47, No. 7), 1997, pp. 816–820.

Abstract of L. Lehtonen et al., "Safety on Levosimendan and other calcium sensitizers", J. Cardiovasc. Pharmacol. (26, Suppl. 1), 1995, pp. 70–76.

Abstract of A. Szewczyk et al., "Mitochondria: a new target for K+ channel openers!", document No. 131:208351, Trends Pharmacol Sci, vol. 20, no. 4, 1999, pp. 157–161.

Abstract of M. Luotolahti et al., "Levosimendan, a calcium sensitizer and potassium channel opener, is safe and improves left ventricular function in acute myocardial infarction" document No. PREV199900514091 Circulation, vol. 98, no. 17, Oct. 27, 1998, pp. 1105–1106.

\* cited by examiner

*Primary Examiner*—Peter O'Sullivan
(74) *Attorney, Agent, or Firm*—Finnegan, Henderson, Farabow, Garrett & Dunner, LLP

(57) ABSTRACT

The use of mitochondrial $K_{ATP}$ channel openers, particularly compounds of general formula (I), for the treatment or prevention of inflammation by inducing apoptosis of inflammatory cells.

5 Claims, 3 Drawing Sheets

ANTI-INFLAMMATORY AGENTS

This application is a U.S. national stage filing of PCT International Application No. PCT/FI01/01000, filed on Nov. 16, 2001. This application also claims the benefit of priority under 35 U.S.C. § 119(a) to Finnish patent application No. 20002525, filed on Nov. 17, 2000.

TECHNICAL FIELD

The present invention relates to the use of mitochondrial $K_{ATP}$ channel openers, such as compounds of general formula (I), for the treatment or prevention of inflammation.

BACKGROUND OF THE INVENTION

Inflammation is caused by the emigration of inflammatory cells such as neutrophils, T-lymphocytes and eosinophils into the tissues, where they are activated. The inflammatory cells are likely to live longer at the site of inflammation due to growth factors and inflammatory mediators produced by the various cells. For instance in bronchial asthma a massive eosinophilia is present. Eosinophils contain cytotoxic granules in their cytoplasm and eosinophil activation/degranulation (lysis) seems to result in epithelial cell damage and airway hyperresponsiveness. Eosinophil survival is prolonged by growth factors such as IL5 and GM-CSF, which inhibit eosinophil apoptosis. Apoptosis is a physiological process of programmed cell death distinct from pathological necrosis. In apoptosis the granule contents of eosinophils are removed without harmful effects characteristic of necrosis (i.e. inflammation and tissue damage).

Apoptosis is chararterised by specific biochemical and morphological changes including cell shrinkage, which may involve $K^+$ efflux, surface blebbing, chromatin condensation and endonuclease-catalyzed DNA fragmentation. Mitochondria are likely to have an important role in regulating apoptotic mechanisms. The evidence is based on the fact that mitochondria contain various proteins that can activate the apoptotic process e.g caspases, cytochrome c, apoptosis inducing factor (AIF). Currently it is believed that a decrease in mitochondrial membrane potential followed by cell shrinkage and generation of reactive oxygen species precede nuclear alterations detected in apoptotic cells.

Agents which are able to open mitochondrial $K_{ATP}$ channels (mitochondrial ATP dependent potassium channels) have been shown to induce mitochondria swelling by lowering the mitochondrial membrane potential (Szewczyk, A. and Marban, E., Trends Pharmacol Sci (1999) 20:157–161). The reduced membrane potential leads to opening of the mitochondrial permeability transition pore leading to volume dysregulation, which may finally cause mitochondrial membrane rupture.

Compounds of general formula (I)

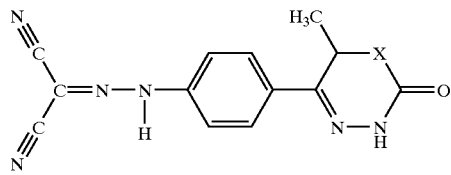

(I)

where X is $CH_2$ or S, have been described in applicant's European Patent No. 383449 B1. The compounds sensitize troponin-C in the heart muscle cells to calcium and are useful in the treatment of congestive heart failure.

The compound of formula (I), where X is $CH_2$, is simendan or [[4-(1,4,5,6-tetrahydro-4-methyl-6-oxo-3-pyridazinyl)phenyl]hydrazono]propanedinitrile. Its optically active enantiomers have been described in applicant's European Patent No. 565546 B1. It was shown that the cardiotonic effects were predominantly due to the (−)-enantiomer of compound (I), i.e. levosimendan.

The effect of simendan to reduce infarct size and arrhythmias has been disclosed in WO 93/21921. It was also shown that the both enantiomers of simendan reduced arrhythmias, and that the (+) enantiomer increased survival. The use of levosimendan for the treatment of pulmonary hypertension has been disclosed in WO 99/66912.

SUMMARY OF THE INVENTION

It has been found that compounds of formula (I)

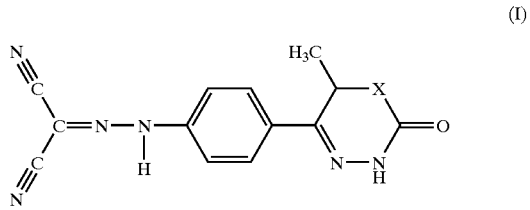

(I)

where X is $CH_2$ or S, and optically active enantiomers thereof are capable of opening mitochondrial $K_{ATP}$ channels and inducing apoptosis of inflammatory cells. Therefore, the compounds are useful in the treatment or prevention of various inflammatory conditions.

Accordingly, the present invention provides a new medical use of a compound of formula (I) or a pharmaceutically acceptable salt thereof in the manufacture of a medicament for use in the treatment or prevention of inflammation.

The present invention also provides use of a mitochondrial $K_{ATP}$ channel opening agent in the manufacture of a medicament for use in the treatment or prevention of inflammation.

The present invention also provides a method for the treatment or prevention of inflammation in a patient, which method comprises administering to a patient in need thereof a therapeutically effective amount of a compound of formula (I) or a pharmaceutically acceptable salt thereof.

The present invention also provides a method for the treatment or prevention of inflammation in a patient, which method comprises administering to a patient in need thereof a therapeutically effective amount of a mitochondrial $K_{ATP}$ channel opening agent.

Furthermore, the present invention provides optically substantially pure (+) enantiomer of compound of formula (I) where X is S, as well as pharmaceutical compositions thereof, such compound and compositions being useful in the treatment or prevention of inflammation.

The inflammation to be treated or prevented according to the present invention is in particular inflammation of the airways associated with bronchial asthma the treatment being independent of bronchodilatation. Other inflammations suitable to be treated or prevented according to the present invention include e.g. rhinitis, myocarditis, inflammatory bowel disease, arthritis, rheumatoid arthritis and inflammation in muscular tissue.

Compounds of formula (I) are preferred agents for the treatment or prevention of inflammation according to the invention. Optically active (+) enantiomers (dextro forms) of the compounds of formula (I) are particularly preferred.

Examples of compounds of formula (I) are:

[[4-(1,4,5,6-tetrahydro-4-methyl-6-oxo-3-pyridazinyl)phenyl]hydrazono]propanedinitrile (simendan) and

[[4-(3,6-dihydro-6-methyl-2-oxo-2H-1,3,4-thiadiazin-5-yl)phenyl]hydrazono]propanedinitrile (compound (I) where X is S).

DETAILED DESCRIPTION OF THE INVENTION

Figure 1A:
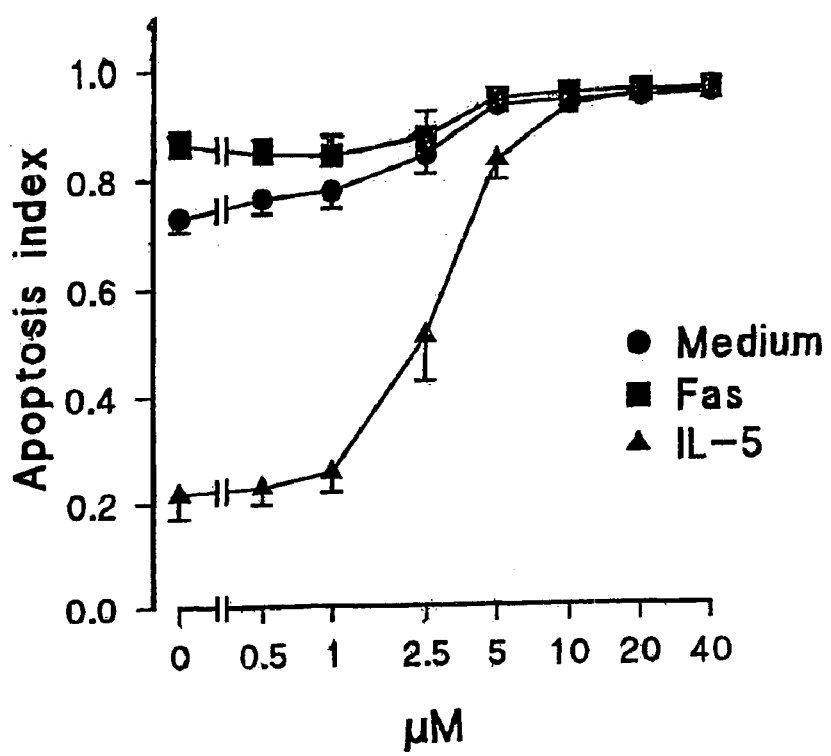
FIG. 1a shows the effect of compound A ($\mu$M) on constitutive (medium) and Fas-induced human eosinophil apoptosis and on reversal of IL-5-afforded eosinophil survival during 40 h in culture.

The term "mitochondrial $K_{ATP}$ channel opening agent" means here a pharmaceutically acceptable compound, which is capable to open mitochondrial ATP dependent potassium channel in a mammal, including a human. The mitochondrial $K_{ATP}$ channel opening activity of a compound can be demonstrated by measuring the decrease of the membrane potential of isolated mitochondria. The method is illustrated in detail in Example 2. Positive result in the test demonstrates a potential usefulness of the compound in the method of the invention.

Mitochondrial $K_{ATP}$ channel opening agents suitable for use in the method of the invention include, but are not limited to compounds of formula (I). In general, any pharmaceutically acceptable mitochondrial $K_{ATP}$ channel opening agent, including those well known in the art, can be used in the method of the invention. Preferably, the mitochondrial $K_{ATP}$ channel opening agent is selective to the mitochondrial $K_{ATP}$ channel over other K channels.

Compounds of formula (I) can be prepared as described in EP 383449 B1 by treating the corresponding amino intermediates with sodium nitrite and malononitrile. Optically active enantiomers of the compounds (I) can be prepared similarly using the optically active amino intermediates as described in EP 565546 B1. Optically substantially pure (+) enantiomers (dextro forms) of the compounds (I) are particularly preferred, since they are devoid of significant hemodynamic effects. The term "optically substantially pure" means here optical purity over about 90%, preferably over 95% and more preferably over 99%. Salts of the compound of the invention can be prepared by known methods. Pharmaceutically acceptable salts are useful as active medicaments, however, preferred are the salts with alkali or alkaline earth metals.

The compound of the invention may be administered in a variety of ways including orally, parenterally, transdermally or by inhalation using conventional forms of preparations, such as capsules, tablets, granules, powders, suppositories, injections, patches, suspensions and syrups. The term "effective amount" means an inflammation inhibiting or preventing amount of compound of the invention. The compound of the invention may be administered periodically or daily or several times a day depending upon the patient's needs. The administration may be systemic or local. The daily dosage may vary depending on the compound to be administered, the age and body weight of the patient, the condition to be treated as well as on the administration method. For example, the compounds of formula (I) may be administered orally to man in daily dose within the range of from about 0.1 mg to about 100 mg, preferably from about 0.5 to about 50 mg. The compounds of the invention may be administered alone or together with other active compounds.

The compositions for the active ingredients can be prepared by the methods commonly employed in the art. In addition to the active compound the compositions may contain pharmaceutically acceptable additives commonly used in the art, such as carriers, binders, excipients, lubricants, suspending agents and diluents. The amount of the active compound in the compositions of the invention is sufficient to produce the desired therapeutic effect, for example, for a compound of formula (I), about 0.1 mg to 100 mg, more preferably from about 0.5 to about 50 mg, in unit dosage for oral, pulmonary or parenteral administration.

EXAMPLE 1

Apoptosis of Eosinophils

Apoptosis was determined in eosinophils isolated from the peripheral blood of apparently healthy volunteers. White blood cells were obtained from whole blood by sedimentation with 3% hydroxyethyl starch, layered on Ficoll and centrifuged. Contaminating red blood cells were lysed by hypotonic treatment. Eosinophils were purified from neutrophils using immunomagnetic anti-CD16 antibody conjugated beads. The obtained eosinophils were cultured for 22–40 h in RPMI 1640 medium supplemented with 10% fetal calf serum plus antibotics.

Eosinophil apoptosis was determined by propidium iodide staining of DNA fragmentation and flow cytometry and confirmed by molphological analysis. Apoptosis index is expressed as (number of apoptotic cells/number of total cells).

Figure 1B:
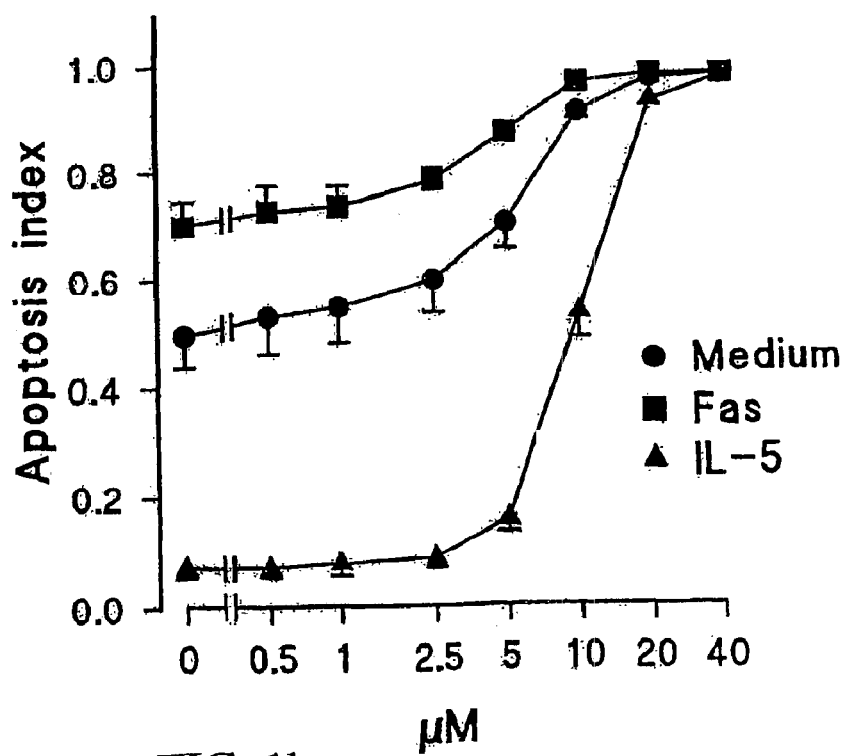
FIG. 1b shows the effect of compound B ($\mu$M) on constitutive (medium) and Fas-induced human eosinophil apoptosis and on reversal of IL-5-afforded eosinophil survival during 40 h in culture.
Figure 2:
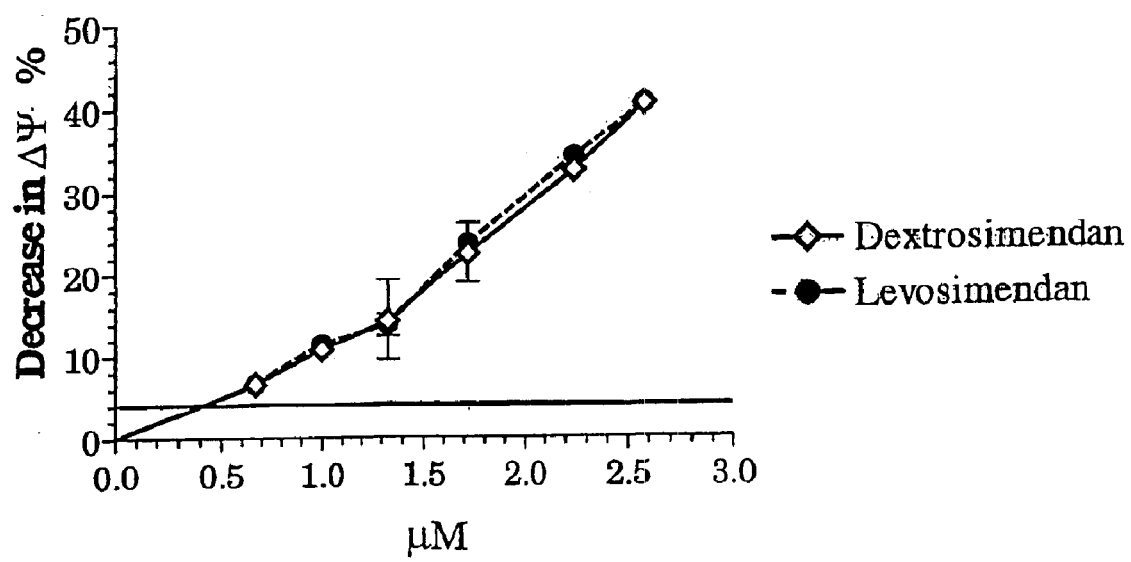
FIG. 2 shows the effect of levosimendan and dextrosimendan ($\mu$M) on membrane potential ($\Delta\Psi$) of rat liver mitochondria respiring only on endogenous substrates in KCl medium.

The effects of compounds A and B were studied:

A. (+)-[[4-(1,4,5,6-tetrahydro-methyl-6-oxo-3-pyridazinyl)phenyl]hydrazono]propanedinitrile (dextrosimendan) and B. (+)-[[4-(3,6-dihydro-6-methyl-2-oxo-2H-1,3,4-thiadiazin-5-yl)phenyl]hydrazono]propanedinitrile The results are shown in FIGS. 1a and 1b. It can be seen that both compounds dose-dependently enhanced constitutive (medium) and Fas-induced human eosinophil apoptosis and reversed IL-5-afforded eosinophil survival during 40 h in culture.

EXAMPLE 2

Mitochondrial ATP Dependent Potassium Channel Opening

In respiring mitochondria, the decrease in $\Delta\Psi$ due to the $K_{ATP}$ channel opening is compensated by an increased respiration rate. When mitochondria respires only on endogenous substrates, and phosphorylation is blocked by oligomycin, the respiration rate is sufficient to generate a high $\Delta\Psi$. However, opening of $K_{ATP}$ channels leads to a decrease in $\Delta\Psi$, which could not be compensated by increased respiration rate. In such a model, opening of $K_{ATP}$ channel is unmasked, and can be recorded. This model was applied to test if opening could be induced by dextrosimendan and levosimendan.

Mitochondria were isolated from rat livers by differential centrifugation in medium containing 210 mM mannitol, 70 mM sucrose, 10 mM Hepes, 1 mM EGTA and 5 mg/ml bovine serum albumin, pH 7.4. The mitochondrial protein concentration was determined by modified Biuret method. Oxygen consumption of isolated liver mitochondria was recorded at 25° C. by means of the Clark-type electrode system in the KCl medium (100 mM KCl, 2 mM $KH_2PO_4$, 10 mM HEPES, 1 mM $MgCl_2$, pH 7.4 with TRIZMA base) or choline chloride medium (100 mM choline chloride, 2 mM $NaH_2PO_4$, 10 mM HEPES, 1 mM $MgCl_2$, pH 7.4 with TRIZMA base). The final mitochondrial protein concentration used in experiments was 1 mg protein/ml. For studies of respiring mitochondria, 5 mM succinate in the presence of 5 $\mu$M rotenone was used as substrate.

Membrane potential ($\Delta\Psi$) of liver mitochondria was measured with rhodamine 123 as a fluorescent probe using the excitation at 503 nm and emission at 527 nm at room temperature with the Hitachi F4000 fluorometer. The difference in fluorescense between mitochondria with addition of FCCP (0.4 $\mu$M) and without it was taken as 100%, and decrease in membrane potential by the tested compounds was expressed in % of FCCP effect.

Dextrosimendan and levosimendan (<2.58 $\mu$M concentration) decreased the $\Delta\Psi$ of rat liver mitochondria, respiring only on endogenous substrates in KCl medium (supplemented with 400 $\mu$M ATP and 1 mg oligomycin/mg protein) and did not significantly change $\Delta\Psi$ in the choline chloride medium.

5-hydroxydecanoate (5-HD), the selective blocker of mitochondrial $K_{ATP}$ channel, abolished the effect of dextrosimendan and levosimendan (not shown). These results indicate that the decrease in $\Delta\Psi$ of mitochondria, respiring only on endogenous substrates, by dextrosimendan and levosimendan is due to the mitochondrial $K_{ATP}$ channel opening.

EXAMPLE 3

Effects on Carrageenan-Induced Paw Edema in Rats

The acute inflammation was induced to the male Wistar rats by an injection of 0.1 ml of 1 or 2% lambda-carrageenan solution into the subplantar tissue of the right hind paw (=1 or 2 mg/paw). Three hours after the carrageenan injection the rats were killed. Both hind paws were cut off just above the heel and weighed. The test compounds (levosimendan and dextrosimendan) were administered orally 30 minutes before the induction of inflammation using dosing levels:

| Levosimendan | 0.1, 1 and 10 mg/kg |
| Dextrosimendan | 10, 30 and 100 mg/kg |

Control rats were included in each experiment. The difference between the weight of the right and the left hind paw was regarded as swelling. 9–10 animals were included in each group.

Figure 3A:
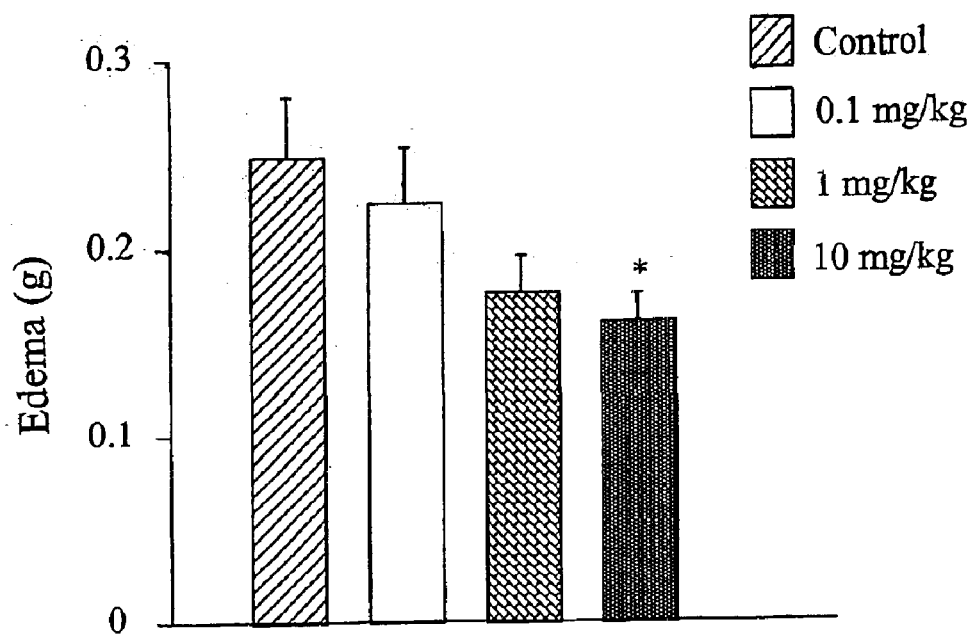
FIG. 3a shows the effect of levosimendan on carrageenan (1 mg)-induced rat paw edema. The vertical bars indicate SEM. *p<0.05, anova and Dunnett's test, n=9–10.
Figure 3B:
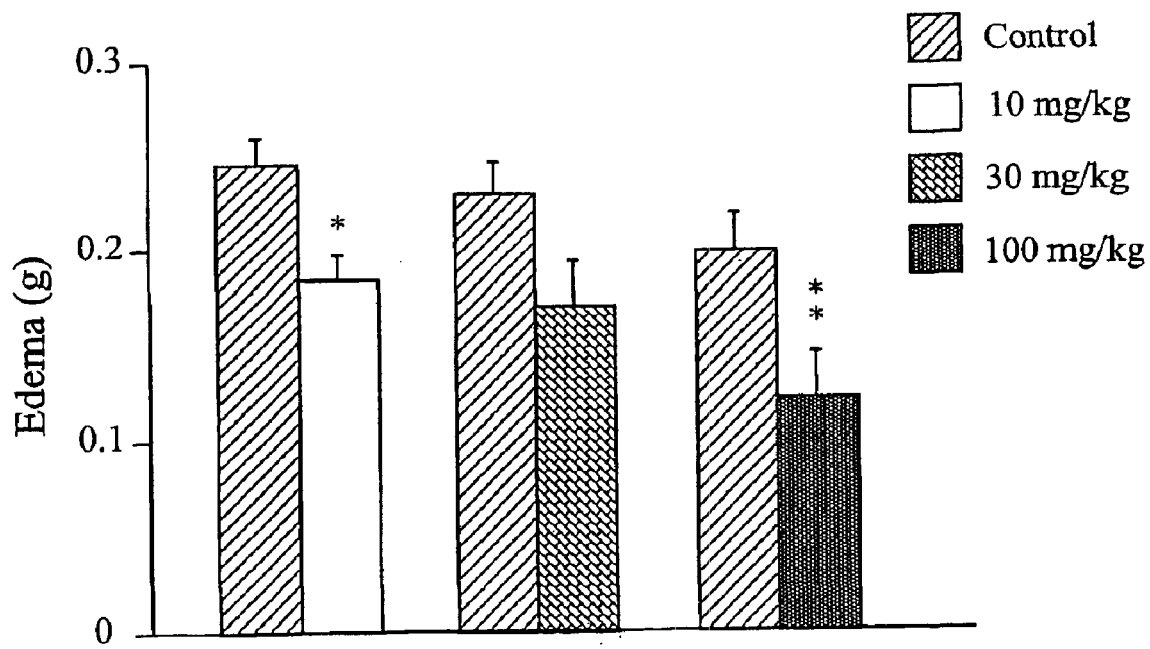
FIG. 3b shows the effect of dextrosimendan on carrageenan (2 mg)-induced rat paw edema. The vertical bars indicate SEM. *p<0.05, **p<0.01, Student's t-test, n=9–10, except 10 mg/kg and control, n=20.

The results are shown in FIGS. 3a (levosimendan) and 3b (dextrosimendan). It can be seen that both levosimendan and dextrosimendan inhibited the carrageenan-induced rat paw edema significantly.

EXAMPLE 4

(+)-[[4-(3,6-dihydro-6-methyl-2-oxo-2H-1,3,4-thiadiazin-5-yl)phenyl]hydrazono]propanedinitrile a) Resolution of rasemic (±)5-(4-aminophenyl)-6-methyl-3,6-dihydro-[1,3,4]-thiadiazin-2-one with dibenzoly-L-tartaric acid (±)5-(4-aminophenyl)-6-methyl-3,6-dihydro-[1,3,4]-thiadiazin-2-one (20.4 g, 0.009 mol) was dissolved in acetonitrile-(816 ml) upon heating. To this solution dibenzoyl-L-tartaric acid (52.0 g, 0.14 mol) was gradually added. The mixture was stirred upon heating until a clear solution was obtained. The solution was then cooled slowly to room temperature with stirring. After being further stirred for 2 h in room temperature the crystalline product was filtered. The enantiomeric purity of the precipitate was checked by HPLC and the recrystallization was repeated in same conditions until the product had the enantiomeric purity over 99.0%. The wet salt was then dissolved in water (150 ml) and potassium carbonate solution (190 g $K_2CO_3$ in 750 ml of water) was added with stirring. The free base was extracted with ethyl acetate, washed with water and evaporated to dryness in vacuo, yielding (+) 5-(4-aminophenyl)-6-methyl-3,6-dihydro-[1,3,4]-thiadiazin-2-one as a crystalline solid (1.34 g) with optical purity 100.0%, chromatographic purity 99.5%, m.p. 216–220° C., $[a]_D^{25}$=+1000°.

b) Preparation of (+)-[[4-(3,6-dihydro-6-methyl-2-oxo-2H-1,3,4-thiadiazin-5-yl)phenyl]hydrazono]propanedinitrile (+) 5-(4-aminophenyl)-6-methyl-3,6-dihydro-[1,3,4]-thiadiazin-2-one (1.34 g, 6 mmol) was dissolved in water (23 ml) and 6 N hydrochloric acid (4.5 ml). The solution was stirred and cooled. A cooled solution of sodiumnitrite (0.5 g) in water (5 ml) was added. Then a cooled solution of malononitrile (0.9 g) in t-butanol (54 ml) was added. In the end to the solution was added a cooled solution of sodium acetate (5.4 g) diluted in water (40 ml). The reaction mixture was stirred under cooling (0° C.) for 3 hours. After stirring the crystalline product was filtered and washed with water, yielding (+)-[[4-(3,6-dihydro-6-methyl-2-oxo-2H-1,3,4-thiadiazin-5-yl)phenyl]hydrazono]propanedinitrile as a crystalline solid (1.7 g) with optical purity of 100%, chromatografic purity 99.3%, m.p. 125–128° C., $[a]_D^{25}$=+1002°.

What is claimed is:

1. A method for the treatment or prevention of inflammation, which comprises administering to a patient in need of the treatment or prevention an effective amount of a compound of formula (I)

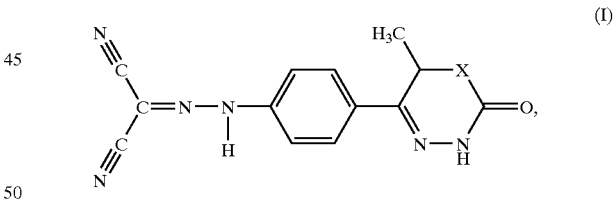

wherein X is $CH_2$ or S, or a pharmaceutically acceptable salt thereof.

2. A method according to claim 1, wherein the inflammation that is treated or prevented is inflammation of the airways associated with bronchial asthma.

3. A method according to claim 1, wherein the inflammation that is treated or prevented is rhinitis, myocarditis, inflammatory bowel disease, arthritis, rheumatoid arthritis or inflammation in muscular tissue.

4. A method according to claim 1, wherein the compound of formula (I) is substantially pure (+) enantiomer.

5. A method according to claim 1, wherein the compound of formula (I) is levosimendan or dextrosimendan.

* * * * *